United States Patent [19]

Petersen et al.

[11] Patent Number: 4,806,539
[45] Date of Patent: Feb. 21, 1989

[54] 1-CYCLOPROPYL-6-FLUORO-1,4-DIHYDRO-4-OXO-7-(1-PIPERAZINYL)-3-QUINOLINECARBOXYLIC ACIDS AND ANTIBACTERIAL AGENTS CONTAINING THEM

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 931,575

[22] Filed: Nov. 17, 1986

[30] Foreign Application Priority Data

Nov. 28, 1985 [DE] Fed. Rep. of Germany ....... 3542002

[51] Int. Cl.⁴ .................... A61K 31/505; C07D 401/10
[52] U.S. Cl. .................. 514/254; 514/235.2; 544/121; 544/225; 544/363; 544/374; 544/379; 544/383; 546/156
[58] Field of Search ....................... 544/363, 121, 225; 514/233, 236, 254

[56] References Cited

U.S. PATENT DOCUMENTS

| | | | |
|---|---|---|---|
| 4,352,803 | 10/1982 | Matsumoto et al. | 544/363 |
| 4,455,310 | 6/1984 | Sakamoto et al. | 544/363 |
| 4,544,658 | 10/1985 | Petersen et al. | 514/254 |
| 4,547,503 | 10/1985 | Petersen et al. | 514/254 |
| 4,559,342 | 12/1985 | Petersen et al. | 514/254 |
| 4,563,459 | 1/1986 | Grohe et al. | 514/254 |
| 4,599,334 | 7/1986 | Petersen et al. | 514/253 |
| 4,659,603 | 4/1987 | Grohe et al. | 514/254 |

FOREIGN PATENT DOCUMENTS

| | | |
|---|---|---|
| 0049355 | 4/1982 | European Pat. Off. |
| 0113092 | 7/1984 | European Pat. Off. |
| 128765 | 10/1981 | Japan ................................ 544/363 |

OTHER PUBLICATIONS

Petersen et al., "Chemical Abstracts", vol. 101, 1984, col. 101:230575z.
Petersen et al., "Chemical Abstracts", vol. 102, 1985, col. 102:62271x.
Grohe et al., "Chemical Abstracts", vol. 101, 1984, col. 101:211165z.
Petersen et al., "Chemical Abstracts", vol. 102, 1985, col. 102:6525w.
Petersen et al., "Chemical Abstracts", vol. 102, 1985, col. 102:6526x.
Petersen et al., "Chemical Abstracts", vol. 104, 1986, col. 104:186447v.
Grohe et al., "Chemical Abstracts", vol. 104, 1986, col. 104:186448w.
Ito et al., "Chemical Abstracts", vol. 104, 1986, col. 104:186451s.
Hokr,, B02, 86-058972/09, J61010-574-A, Pharmaceuticals, p. 8, Week 8609.

Primary Examiner—Glennon H. Hollrah
Assistant Examiner—James H. Turnipseed
Attorney, Agent, or Firm—Sprung Horn Kramer & Woods

[57] ABSTRACT

An antibacterial 1-cyclopropyl-6-fluoro-1,4-dihydro-4-oxo-7-(1-piperazinyl)-3-quinolinecarboxylic acid of the formula

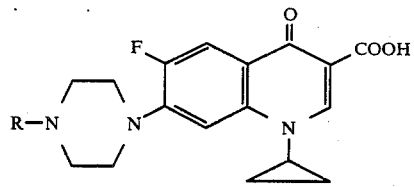

in which R represents branched or straight-chain propyl or butyl which is optionally substituted by hydroxy or methoxy, unsubstituted tert.-butyl, 2-methylthioethyl, trifluoromethylthiomethyl, 2-trifluoromethylthioethyl, cycloalkyl with 3 to 6 carbon atoms, cycloalkenyl having 5 to 6 carbon atoms optionally substituted by hydroxyl, 1,1-dioxidotetrahydrothiophen-3-yl, cyclopropylmethyl, 1-phenethyl, furylmethyl, allyl or propargyl optionally substituted by phenyl and their pharmaceutically usable hydrates, acid addition salts, metal and guanidinium salts and prodrug forms.

5 Claims, No Drawings

1-CYCLOPROPYL-6-FLUORO-1,4-DIHYDRO-4-OXO-7-(1-PIPERAZINYL)-3-QUINOLINECARBOXYLIC ACIDS AND ANTIBACTERIAL AGENTS CONTAINING THEM

The invention relates to new 1-cyclopropyl-6-fluoro-1,4-dihydro-4-oxo-7-(1-piperazinyl)-3-quinolinecarboxylic acids which are substituted in the piperazine part, processes for their preparation and antibacterial agents containing them.

It has been disclosed that 1-cyclopropyl-6-fluoro-1,4-dihydro-4-oxo-7-(1-piperazinyl)-3-quinolinecarboxylic acids can be used as antimicrobial active compounds (European Patent Application No. 49,355 and German Patent Application No. 3,142,854).

It has now been found that the new 1-cyclopropyl-6-fluoro-1,4-dihydro-4-oxo-7-(1-piperazinyl)-3-quinolinecarboxylic acids substituted in the piperazine part, of the formula (I)

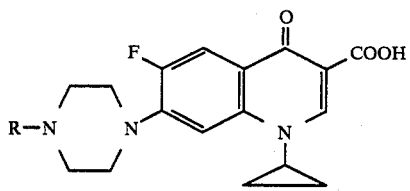

in which R represents branched or straight-chain propyl which is di- or trisubstituted by hydroxyl or methoxy, or branched or straight-chain butyl which is mono-, di- or trisubstituted by hydroxyl or methoxy, or represents unsubstituted tert.-butyl, or furthermore represents 2-methylthioethyl, trifluoromethylthiomethyl, 2-trifluoromethylthioethyl, cycloalkyl with 3 to 6 carbon atoms, cycloalkenyl which has 5 or 6 carbon atoms and is optionally substituted by hydroxyl, 1,1-dioxidotetrahydrothiophen-3-yl, cyclopropylmethyl, 1-phenethyl or furylmethyl, or represents allyl or propargyl which is optionally substituted by phenyl, and pharmaceutically usable hydrates, acid addition salts and alkali metal, alkaline earth metal, silver and guanidinium salts thereof, and the compounds in the form of their esters and in other customary prodrug forms, have a powerful antibacterial action.

They are therefore suitable as active compounds for human and veterinary medicine, veterinary medicine also including the treatment of fish for therapy or prevention of bacterial infections.

Preferred compounds of the formula (I) are those in which R represents branched or straight-chain propyl which is di- or trisubstituted by hydroxyl or methoxy, or branched or straight-chain butyl which is mono-, di- or trisubstituted by hydroxyl or methoxy, or represents unsubstituted tert.-butyl, or furthermore represents trifluoromethylthiomethyl, 2-trifluoromethylthioethyl, cycloalkyl with 3 to 6 carbon atoms, cyclohexenyl which is optionally substituted by hydroxyl, 1,1-dioxidotetrahydrothiophen-3-yl, cyclopropylmethyl or furylmethyl, or represents allyl or propargyl which is optionally substituted by phenyl.

Prodrugs here are to be understood as compounds which carry a radical bonded in ester form via the carboxyl group of the quinolone-3-carboxylic acids according to the invention and release the active compound molecule again in the body, this radical being split off. By such prodrug formation, it is possible, inter alia, to increase the bioavailability of active compounds [see also Pharmazie 38, 663 (1983)].

In addition to the simple methyl and ethyl esters of the quinolone-3-carboxylic acids according to the invention, it is also possible to prepare the following prodrugs of the compounds of the formula (I) which carry a customary prodrug radical E:

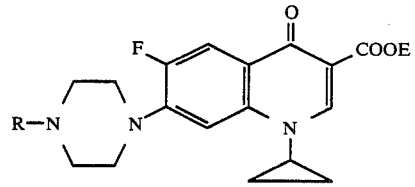

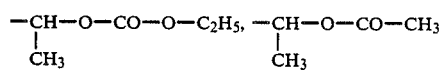

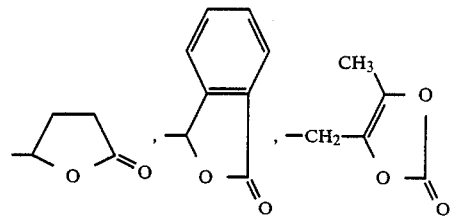

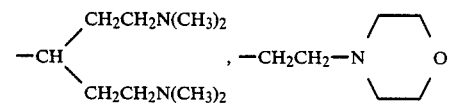

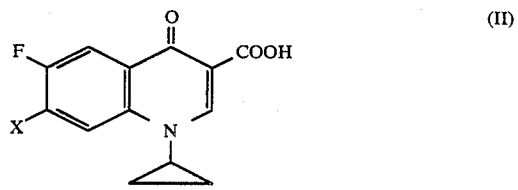

It has furthermore been found that the compounds of the formula (I) are obtained by a process in which a compound of the formula (II)

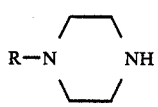

in which
X represents fluorine or chlorine, is reacted with piperazine derivatives of the formula (III)

R—N⟨ ⟩NH         (III)

in which
R has the abovementioned meaning, if appropriate in the presence of acid-binding agents (method A).

Compounds of the formula (I) according to the invention can also be obtained by a process in which 1-cyclopropyl-6-fluoro-1,4-dihydro-4-oxo-7-(1-piperazinyl)-3-quinolinecarboxylic acid of the formula (IV)

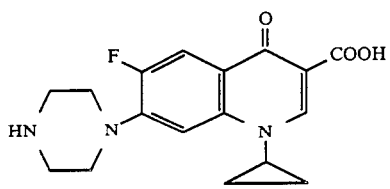

is reacted with compounds of the formula (V)

R—Y  (V)

in which
R has the abovementioned meaning but cannot be tert.-butyl, tris(hydroxymethyl)-methyl or cycloalkyl, and
Y denotes halogen, in particular chlorine, bromine or iodine,
if appropriate in the presence of acid-binding agents (method B).

If 1-cyclopropyl-6,7-difluoro-1,4-dihydro-4-oxo-3-quinolinecarboxylic acid and N-(tert.-butyl)-piperazine are used as starting substances in the reaction according to method A, the course of the reaction can be represented by the following equation:

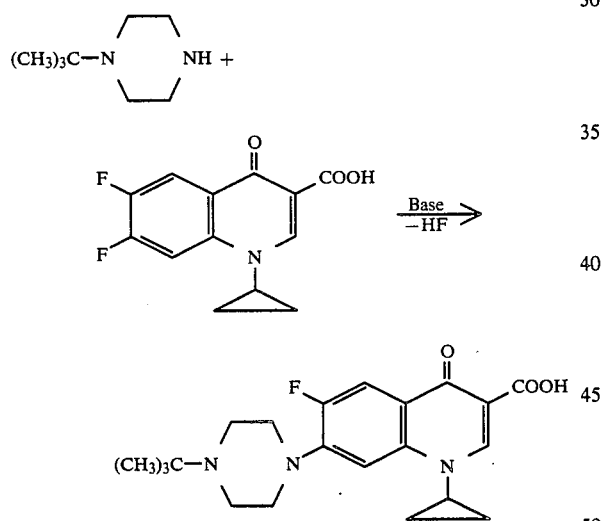

If, for example, 1-cyclopropyl-6-fluoro-1,4-dihydro-4-oxo-7-(1-piperazinyl)-3-quinolinecarboxylic acid and allyl bromide are used as starting substances in the reaction according to method B, the course of the reaction can be represented by the following equation:

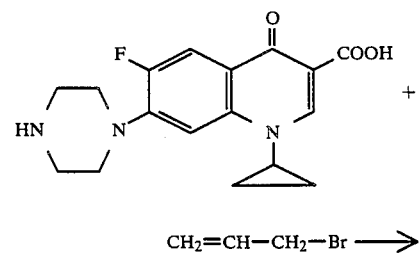

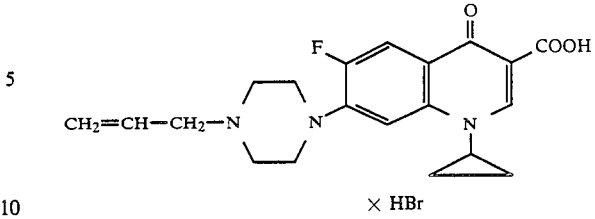

The 7-chloro-1-cyclopropyl-6-fluoro-1,4-dihydro-4-oxo-3-quinolinecarboxylic acid (German Patent Application No. 3,142,854) used as the starting substance according to method A and the 1-cyclopropyl-6,7-difluoro-1,4-dihydro-4-oxo-3-quinolinecarboxylic acid (European Patent Application No. 113,091) are known.

The piperazine derivatives of the formula (III) used as starting substances according to method A are known in some cases, or can be prepared by the following process.

The reaction of bis-(2-hydroxyethyl)-amine (1) with 2-nitrophenylsulphenyl chloride (NPS-Cl) leads to N-(2-nitrophenylsulphenyl)-bis-(2-hydroxyethyl)-amine (2), which is reacted with 4-toluenesulphonyl chloride to give the bis-sulphonate (3). (3) can be cyclized to give the NPS-protected piperazine derivatives (4) by heating with primary amines in a solvent, such as, for example, isopropanol, in the presence of excess amine or an auxiliary base, such as potassium carbonate. After the NPS protective group has been split off with 2-mercaptobenzothiazole/hydrochloric acid, the corresponding piperazine derivative is obtained as the bis-hydrochloride (5), from which the piperazine derivatives (3) can be prepared as free bases with alkali metal hydroxides.

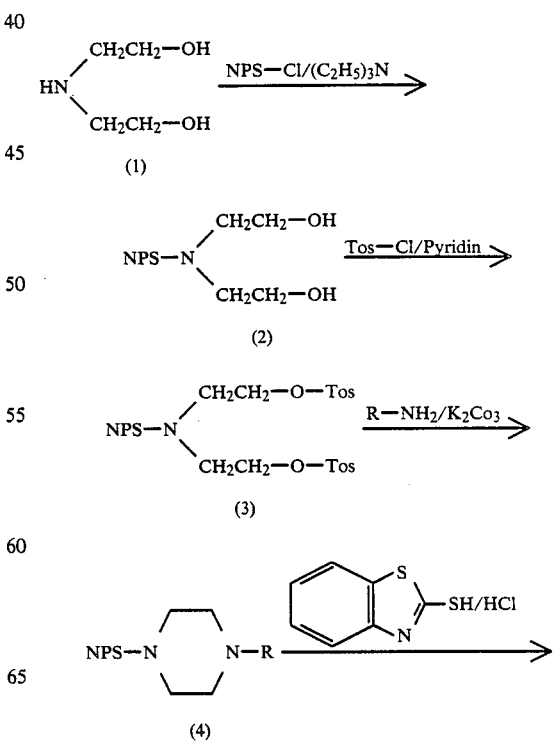

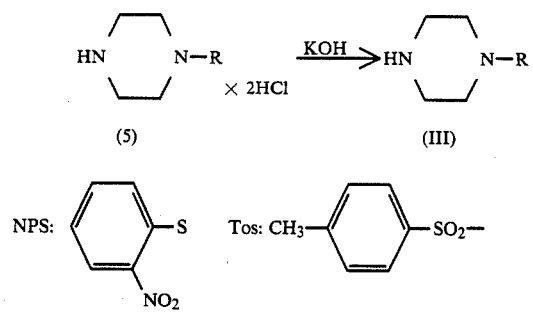

Examples which may be mentioned of compounds of the formula (III) are:

1-(tert.-butyl)-piperazine, 1-[tris-(hydroxymethyl)methyl]-piperazine, 1-(1-phenylethyl)-piperazine, 1-cinnamyl-piperazine, 1-cyclopropyl-piperazine, 1-cyclobutylpiperazine, 1-cyclopentyl-piperazine, 1-cyclohexyl-piperazine, 1-(2-furylmethyl)-piperazine, 1-(3-furylmethyl)piperazine and 1-(1,1-dioxido-tetrahydrothiophen-3-yl)piperazine.

Particular piperazine derivatives of the formula (III) are prepared by a process in which piperazine (6) is reacted with an epoxide to give a mixture of mono- and bis-substitution product and the desired mono-substituted piperazine is separated off by chromatography. The reaction of piperazine with 4,4-dimethyl-3,5,8-trioxabicyclo[5,1,0]octane (7) (J. Org. Chem. 41, 2469 [1976] in the equation may be mentioned as an example:

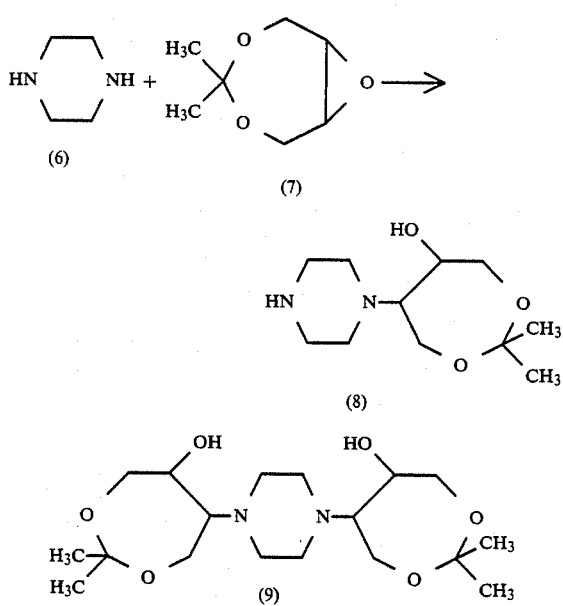

1-(6-Hydroxy-3-cyclohexenyl)-piperazine is obtained analogously with 1,4-cyclohexadiene monoepoxide.

Hydrolysis of (8) with dilute hydrochloric acid leads to 1-(1,3,4-trihydroxy-2-butyl)-piperazine, the isopropylidene group being split off.

The 1-cyclopropyl-6-fluoro-1,4-dihydro-4-oxo-7-(1-piperazinyl)-3-quinolinecarboxylic acid of the formula (IV) used as the starting compound according to method B is known from German Patent Application No. 3,142,854.

The halogen compounds of the formula (V) used as starting compounds according to method B are known or can be prepared by known methods. Examples which may be mentioned are: 4-hydroxybutyl chloride, trifluoromethylthiomethyl chloride, 2-trifluoromethylthioethyl bromide, allyl bromide, propargyl chloride, benzyl bromide, cyclopropylmethyl chloride and α-methylbenzyl bromide.

The reaction of (II) with (III) according to method A, in which the piperazine derivatives (III) can also be employed in the form of their hydrochlorides, is preferably carried out in a diluent, such as dimethyl sulphoxide, N,N-dimethylformamide, hexamethyl-phosphoric acid triamide, sulpholane, acetonitrile, water, an alcohol, such as methanol, ethanol, n-propanol or isopropanol, glycol monomethyl ether or pyridine. Mixtures of these diluents can also be used.

All the customary inorganic and organic acid-binding agents can be used as the acid-binding agents. These include, preferably, the alkali metal hydroxides, alkali metal carbonates, organic amines and amidines. Particularly suitable agents which may be mentioned specifically are: triethylamine, 1,4-diazabicyclo[2,2,2]octane (DABCO), 1,8-diazabicyclo[5,4,0]undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure, but also under increased pressure. The reaction is in general carried out under pressures between about 1 and 100 bar, preferably between 1 and 100 bar.

In carrying out the process according to the invention, 1 to 15 mol, preferably 1 to 6 mol, of the piperazine (III) are employed per mol of the quinolinecarboxylic acid (II).

Free hydroxyl groups can be protected during the reaction by a suitable hydroxy-protective group, for example by the isopropylidene group or the tetrahydropyranyl radical, and liberated again when the reaction has ended.

The reaction of (IV) with (V) is preferably carried out in a diluent, such as dimethyl sulphoxide, dioxane, N,N-dimethylformamide, hexamethyl-phosphoric acid triamide, sulpholane, water, an alcohol, such as methanol, ethanol, n-propanol or isopropanol, glycol monomethyl ether or pyridine. Mixtures of these diluents can also be used.

All the customary inorganic and organic acid-binding agents can be used as acid-binding agents. These include, preferably, the alkali metal hydroxides, alkali metal carbonates, organic amines and amidines. Particularly suitable agents which may be mentioned specifically are: triethylamine, 1,4-diazabicyclo[2,2,2]octane (DABCO) or 1,8-diazabicyclo[5,4,0]undec-7-ene (DBU).

Phase transfer catalysts, such as tetrabutylammonium bromide, tetrabutylammonium chloride or benzyl-triethyl-ammonium chloride, can be added to accelerate the reaction.

The reaction temperatures can be varied within a substantial range. The reaction is in general carried out between about 20° and about 180° C., preferably between 40° and 110° C.

The reaction can be carried out under normal pressure, but also under increased pressure. The reaction is in general carried out under pressures between about 1 and about 100 bar, preferably between 1 and 10 bar.

In carrying out the process according to the invention in method B, 1 to 4 mol, preferably 1 to 1.5 mol, of the compound (V) are employed per mol of the compound (IV).

The acid addition salts of the compounds according to the invention are prepared in the customary manner, for example by dissolving the betaine in excess aqueous acid and precipitating the salt with a water-miscible organic solvent, such as methanol, ethanol, acetone or acetonitrile. It is also possible to heat equivalent amounts of betaine and acid in water until a solution is obtained and then to evaporate the solution to dryness. The salts of hydrochloric acid, sulphuric acid, acetic acid, glycolic acid, lactic acid, succinic acid, citric acid, tartaric acid, methanesulphonic acid, galacturonic acid, gluconic acid, embonic acid, glutamic acid or asparaginic acid, for example, are to be understood as pharmaceutically usable salts.

The alkali metal or alkaline earth metal salts are obtained, for example, by dissolving the betaine in less than the equivalent amount of alkali metal hydroxide solution or alkaline earth metal hydroxide solution, filtering off the undissolved betaine and evaporating the filtrate to dryness. Sodium, potassium or calcium salts are pharmaceutically suitable. By reacting an alkali metal salt or alkaline earth metal salt with a suitable silver salt, such as silver nitrate, the corresponding silver salts of the 1,4-dihydro-4-oxo-quinoline-3-carboxylic acids are obtained.

In addition to the compounds listed in the examples, new active compounds which may be mentioned specifically are:

1-cyclopropyl-6-fluoro-1,4-dihydro-4-oxo-7-[4-(1-phenylethyl)-1-piperazinyl]-3-quinolinecarboxylic acid,
7-(4-benzhydryl-1-piperazinyl)-1-cyclopropyl-6-fluoro-1,4-dihydro-4-oxo-3-quinolinecarboxylic acid,
1-cyclopropyl-6-fluoro-1,4-dihydro-7-{4-[tris-(hydroxymethyl)methyl]-1-piperazinyl}-4-oxo-3-quinolinecarboxylic acid,
7-(4-cyclobutyl-1-piperazinyl)-1-cyclopropyl-6-fluoro-1,4-dihydro-4-oxo-3-quinolinecarboxylic acid,
7-(4-cyclopentyl-1-piperazinyl)-1-cyclopropyl-6-fluoro-1,4-dihydro-4-oxo-3-quinolinecarboxylic acid,
1-cyclopropyl-6-fluoro-1,4-dihydro-7-[4-(1-hydroxy-2-propyl)-1-piperazinyl]-4-oxo-3-quinolinecarboxylic acid,
1-cyclopropyl-6-fluoro-1,4-dihydro-7-[4-(1-methoxy-2-propyl)-2-piperazinyl]-4-oxo-3-quinolinecarboxylic acid.

EXAMPLE OF A TABLET ACCORDING TO THE INVENTION

| Each tablet contains: | |
| --- | --- |
| Compound of Example 1 | 583.0 mg |
| Microcrystalline cellulose | 55.0 mg |
| Maize starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| The lacquer coating contains: | |
| Poly-(O—hydroxypropyl-O—methyl)-cellulose 15 cp | 6.0 mg |
| Macrogol 4000 recommended INN polyethylene glycols (DAB) | 2.0 mg |
| Titanium-(IV) oxide | 2.0 mg |
| | 10.0 mg |

The compounds according to the invention exhibit a broad antibacterial action against Gram-positive and Gram-negative germs, in particular against Enterobacteriaceae; above all against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibres, leather, paper and wood, and foodstuffs and water.

The compounds according to the invention are active against a very broad spectrum of microorganisms. With their aid, it is possible for Gram-negative and Gram-positive bacteria and bacteria-like microorganisms to be combated and the diseases caused by these pathogens to be prevented, alleviated and/or cured.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases caused by the following pathogens or by mixtures of the following pathogens can be treated and/or prevented: Gram-positive cocci, for example Staphylococci (*Staph. aureus* and *Staph. epidermidis*) and Streptococci (*Strept, agalactiae, Strept. facecalis, Strept. pneumoniae* and *Strept. pyogenes*); Gram-negative cocci (*Neisseria gonorrhoeae*) and Gram-negative rod-shaped bacilli, such as Enterobacteriaceae, for example *Escherichia coli, Haemophilus influenzae,* Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. macrcescens*), Proteus (*Pr. mirabilis, Pr. rettgeri* and *Pr. vlugaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis*, representatives of the genus Peptococcus, Peptostreptococcus and the genus Clostridium; and furthermore mycoplasma (*M. pneumoniae, M. hominis* and *M. urealyticum*) and mycobacteria, for example *Mycobacterium tuberculosis*.

The above list of pathogens is purely by way of example and is in no way to be interpreted as limiting. Examples which may be mentioned of diseases which can be caused by the pathogens mentioned or by mixed infections can be prevented, alleviated or cured by the compounds according to the invention are:

infectious diseases in humans, such as, for example, otitis, pharyngitis, pneumonia, peritonitis, pyelonephritis, cystitis, endocarditis, systemic infections, bronchitis, acute and chronic, septic infections, diseases of the upper respiratory tract, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, postoperative wound infections, abscesses, phlegmon, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid fever, meningitis and infections of the nervous system, salpingitis, endometritis, genital infections, pelveoperitonitis and eye infections.

As well as on humans, bacterial infections can also be treated in other species. Examples which may be mentioned are:

pigs: *Coli diarrhoea*, enterotoxaemia, spsis, dysentery, salmonellosis, metritis-mastitis-agalactiae syndrome and mastitis;

ruminants (cattle, sheep, goats): diarrhoea, sepsis, bronchopneumonia, salmonellosis, pasteurellosis, mycoplasmosis and genital infections;

horses: bronchopneumonia, joint ill, puerperal and postpuerperal infections and salmonellosis;

dogs and cats: bronchopneumonia, diarrhoea, dermatitis, otitis, urinary tract infections and prostatitis;

and poultry (chicken, turkeys, quail, pigeons, ornamental birds and others): mycoplasmosis, *E. coli* infections, chronic respiratory tract diseases, salmonellosis, pasteurellosis and psittacosis.

Bacterial infections can also be treated in the rearing and management of stock and ornamental fish, the antibacterial spectrum being extended beyond the abovementioned pathogens to other pathogens, such as, for example, Pasteurella, Brucella, Camphylobacter, Listeria, Erysipelothrix, Corynebacteria, Borellia, Treponema, Nocardia, Rickettsia and Yersinia.

The present invention includes pharmaceutical formulations which, in addition to non-toxic, inert pharmaceutically suitable excipients, contain one or more compounds according to the invention, or which consist of one or more active compounds according to the invention, and processes for the preparation of these formulations.

The present invention also includes pharmaceutical formulations in dosage units. This means that the formulation is in the form of individual parts, for example tablets, coated tablets, capsules, pills, suppositories and ampoules, the active compound content of which corresponds to a fraction or to a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, ½, ⅓ or ¼ of a daily dose.

Non-toxic, inert pharmaceutically suitable excipients are to be understood as meaning solid, semi-solid or liquid diluents, fillers and formulation auxiliaries of all types.

Tablets, coated tablets, capsules, pills, granules, suppositories, solutions, suspensions and emulsions, pastes, ointments, gels, creams, lotions, powders and sprays may be mentioned as preferred pharmaceutical formulations.

Tablets, coated tablets, capsules, pills and granules can contain the active compound or compounds in addition to the customary excipients such as (a) fillers and extenders, for example starches, lactose, sucrose, glucose, mannitol and salicic acid, (b) binders, for example carboxymethylcellulose, alginates, gelatin and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, coated tablets, capsules, pills and granules can be provided with the customary coatings and shells, if appropriate containing opacifying agents, and can also be of such composition that they release the active compound or compounds only or preferentially in a certain part of the intestinal tract, optionally in a delayed manner, examples of embedding compositions which may be used being polymeric substances and waxes.

The active compound or compounds can also be in microencapsulated form, if appropriate with one or more of the abovementioned excipients.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives which improve the taste and small, for example peppermint oil an eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds, in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally and locally (powders, ointments and drops), and for therapy of infections in hollow cavities and body cavities. Possible suitable formulations are injection solutions, solutions and suspensions for oral therapy, gels, infusion formulations, emulsions, ointments or drops. Of pharmacological and dermatological formulations, silver salts and other salts, ear drops, eye drops, powders or solutions can be used for local therapy. In the case of animals, intake can also be via the feed or drinking water in suitable formulations. It is furthermore possible to use gels, powders, dusts, tablets, controlled release tablets, premixes, concentrates, granules, pellets, tablets, boli, capsules, aerosols, sprays and inhalates on humans and animals. The compounds according to the invention can furthermore be incorporated into other carrier materials, such as, for example, plastics (chains of plastic for local therapy), collagen or bone cement.

In general it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual administrations, to achieve the desired results. An individual administration preferably contains the active compound or compounds according to the invention in amounts of about 1 to about 80, in particular 3 to 30, mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus in some cases it may suffice to manage with less than the abovementioned amount of active compound whilst in other cases the abovementioned amount of active compound must be exceeded. The particular optimum dosage and mode of administration of the active compounds can easily be determined by any expert on the basis of his expert knowledge.

The new compounds can be administered in the customary concentrations and formulations together with the feed or with feed formulations or with the drinking water. An infection by Gram-negative or Gram-positive bacteria can thereby be prevented, alleviated and/or cured, and a promotion of growth and an improvement in feed utilization can thereby be achieved.

PREPARATION OF THE STARTING COMPOUNDS

Example A

N-(2-Nitrophenylsulphenyl)-bis-(2-hydroxyethyl)-amine (2)

A solution of 379 g (2 mol) of 2-nitrophenylsulphenyl chloride in 2 l of methylene chloride is added to a solution of 210 g (2 mol) of bis(2-hydroxyethyl)amine and 202 g (2 mol) of triethylamine in 3 l of methylene chloride in the course of 90 minutes, the temperature rising from 21° to 34°. The mixture is subsequently stirred at room temperature for 2 hours and is left to stand overnight and the solution is washed six times with 1 l of water each time, dried with sodium sulphate and concentrated in vacuo. The residue is an orange-yellow solid product of melting point 82°–86°, which is sufficiently pure for further reaction. Yield: 499 g.

Example B

N-(2-Nitrophenylsulphenyl)-bis[2-(4-toluenesulphonyloxy)ethyl]-amine (3)

389 g (1.5 mol) of crude N-(2-nitrophenylsulphenyl)-bis(2-hydroxyethyl)-amine are dissolved in 2 l of absolute pyridine, and 580 g (3 mol) of 4-toluenesulphonyl chloride are added at −10° in the course of 20 minutes. The mixture is stirred at −5° to 0° for 4 hours and left to stand at 0° overnight, and 4 l of water are added. Thereafter, the mixture is extracted with 3×1 l of methylene chloride and the extract is washed with 7×1 l of water, dried with sodium sulphate and concentrated. The oily residue is stirred with 1 l of a mixture of acetonitrile/methanol (1:1), a solid product precipitating, which is filtered off with suction with methanol. Yield: 423.6 g of melting point 91°–93°.

Example C

1-Cyclopropyl-4-(2-nitrophenylsulphenyl)-piperazine

A mixture of 112 g (0.198 mol) of N-(2-nitrophenylsulphenyl)-bis[2-(4-toluenesulphonyloxy)-ethyl]amine, 16.7 g (0.29 mol) of cyclopropylamine and 82 g (0.6 mol) of powdered potassium carbonate in 3.3 l of isopropanol is heated under reflux for 6 hours. Thereafter, the mixture is concentrated in vacuo, the residue is taken up in 550 ml of methylene chloride and the mixture is washed with water, dried with sodium sulphate and concentrated. For purification, the crude product is filtered over 600 g of silica gel with methylene chloride as the mobile phase and the eluate is concentrated. Yield: 47 g of melting point 100°–102°.

The following 1-substituted 4-(2-nitrophenylsulphenyl)-piperazines(4) are obtained analogously:

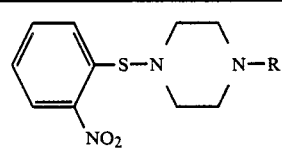
(4)

| R | Melting point |
|---|---|
| (CH$_3$)$_3$C | 103–105° |
| (HO—CH$_2$)$_3$C | 179–182° |

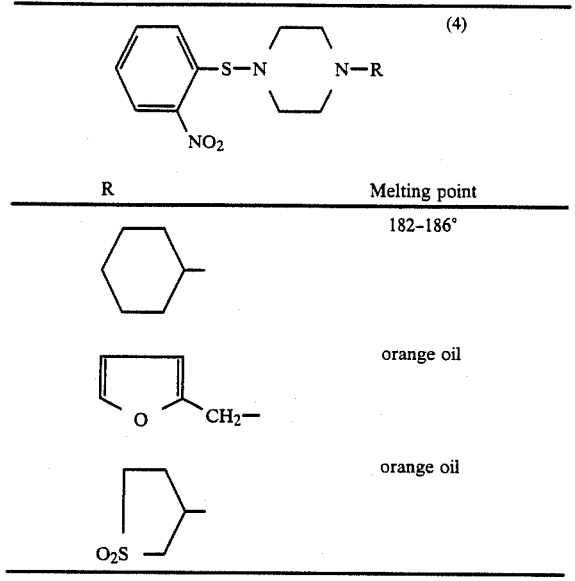

| R | Melting point |
|---|---|
| cyclohexyl | 182–186° |
| furfuryl (CH₂-furan) | orange oil |
| O₂S (sulfolanyl) | orange oil |

Example D

1-Cyclopropyl-piperazine

A solution of 11.3 g (68 mmol) of 2-mercaptobenzothiazole in 80 ml of methylene chloride/40 ml of methanol is added to a solution of 19 g (68 mmol) of 1-cyclopropyl-4-(2-nitrophenyl)-piperazine in 135 ml of methylene chloride and the mixture is then acidified with 136 ml of 1N hydrochloric acid. The mixture is extracted with 3 times 50 ml of water, the combined aqueous phases are concentrated and the residue is suspended in a little ethanol, filtered off with suction and dried. Yield: 12.8 g (96.5% of theory) of 1-cyclopropyl-piperazine dihydrochloride of melting point about 250° (with decomposition) (already discolours from about 210°).

To prepare the free 1-cyclopropyl-piperazine, 11.9 g of the dihydrochloride are stirred with a solution of 8.4 g of potassium hydroxide in 60 ml of methanol at room temperature for 3 hours and the undissolved potassium chloride is filtered off with suction. The methanol is distilled off from the mother liquor under normal pressure and the residue is distilled in vacuo. Yield: 7.0 g (92.6% of theory) of 1-cyclopropyl-piperazine of boiling point 50°/12 mbar.

The following 1-substituted piperazine dihydrochlorides (5) and 1-substituted piperazines (III) are obtained analogously:

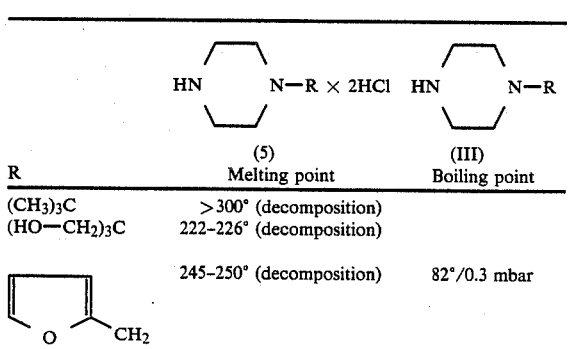

| R | (5) Melting point | (III) Boiling point |
|---|---|---|
| (CH₃)₃C | >300° (decomposition) | |
| (HO—CH₂)₃C | 222–226° (decomposition) | |
| furfuryl (O-CH₂-) | 245–250° (decomposition) | 82°/0.3 mbar |

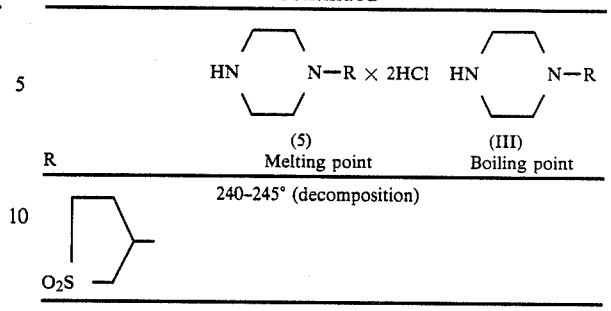

| R | (5) Melting point | (III) Boiling point |
|---|---|---|
| sulfolanyl (O₂S-) | 240–245° (decomposition) | |

Example E

1-(6-Hydroxy-2,2-dimethyl-1,3-dioxepan-5-yl)-piperazine 14.4 g (0.1 mol) of 4,4-dimethyl-3,5,8-trioxabicyclo[5.1.0]octane (J. Org. Chem. 41, 2469 [1976]) are heated under reflux in 100 ml of acetonitrile with 20 g (0.1 mol) of piperazine hexahydrate for 8 hours and the 1,4-bis-(6-hydroxy-2,2-dimethyl-1,3-dioxepan-5-yl)-piperazine precipitated [melting point: 235°–237° (from isopropanol)] is filtered off with suction. The mother liquor is concentrated and the residue is purified by chromatography on 200 g of silica gel with methylene chloride/methanol (9:1) as the mobile phase, the main component being eluted towards the end of the chromatography with methylene chloride/methanol (4:1). 4.7 g of 1-(6-hydroxy-2,2-dimethyl-1,3-dioxepan-5-yl)-piperazine are obtained as an oil; R_f value=0.05 (on silica gel; methylene chloride/methanol (9:1)].

Example F

1-(6-Hydroxy-3-cyclohexen-1-yl)-piperazine 1-(6-Hydroxy-3-cyclohexen-1-yl)-piperazine of melting point 58°–64° is obtained, alongside 1,4-bis(6-hydroxy-3-cyclohexen-1-yl)-piperazine (melting point=207°–209°), analogously to Example E with 1,4-cyclohexadiene monoepoxide.

Example 1

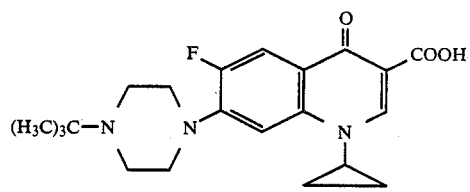

2.2 g (20 mmol) of 1,4-diazabicyclo[2,2,2]octane are added to a mixture of 1.33 g (5 mmol) of 1-cyclopropyl-6,7-difluoro-1,4-dihydro-4-oxo-3-quinolinecarboxylic acid and 1.1 g (5 mmol) of 1-(tert.-butyl)piperazine dihydrochloride in 12.5 ml of pyridine, and the mixture is heated under reflux for 3 hours. It is concentrated in vacuo, the residue is stirred with 25 ml of water and the pH is brought to 5 with 2N hydrochloric acid. The precipitate which has separated out is filtered off with suction, washed with water and recrystallized from glycol monomethyl ether. 1.45 g (75% of theory) of 7-(4-tert.-butyl-1-piperazinyl)-1-cyclopropyl-6-fluoro-1,4-dihydro-4-oxo-3-quinolinecarboxylic acid of melting point 257°–260° are obtained.

Example 2

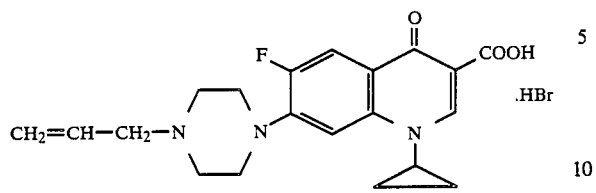

3.3 g (10 mmol) of 1-cyclopropyl-6-fluoro-1,4-dihydro-4-oxo-7-(1-piperazinyl)-3-quinolinecarboxylic acid are heated at 60° C. in 50 ml of dimethylformamide with 1.8 g (15 mmol) of allyl bromide and 2.1 g of triethylamine for 8 hours. The mixture is concentrated in vacuo, the residue is stirred with 30 ml of water and the precipitate is filtered off with suction, washed with methanol and dried. 2.2 g of 7-(4-allyl-1-piperazinyl)-1-cyclopropyl-6-fluoro-1,4-dihydro-4-oxo-3-quinolinecarboxylic acid hydrobromide of melting point 295°–298° (with decomposition) are obtained; after recrystallization from water, 1.5 g of melting point 300°–302° (with decomposition) are isolated.

Example 3

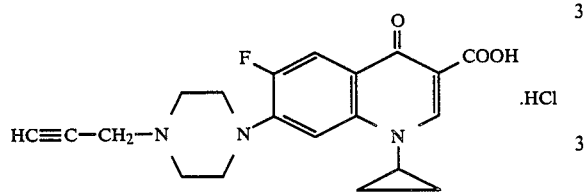

1-Cyclopropyl-6-fluoro-1,4-dihydro-4-oxo-7-(4-propargyl-1-piperazinyl)-3-quinolinecarboxylic acid hydrochloride of melting point 237°–240° (with decomposition) are obtained analogously to Example 2 with propargyl chloride.

Example 4

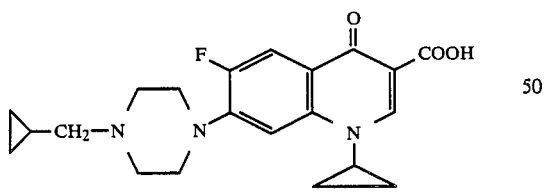

3.3 g (10 mmol) of 1-cyclopropyl-6-fluoro-1,4-dihydro-4-oxo-7-(1-piperazinyl)-3-quinolinecarboxylic acid are heated at 90° in 50 ml of dimethylformamide with 1.8 g (20 mmol) of chloromethylcyclopropane, 3.3 g (20 mmol) of potassium iodide and 2.1 g of triethylamine for 5 hours. The solution is poured into 40 ml of water, the pH is brought to 5 with 2N hydrochloric acid and the precipitate is filtered off with suction and recrystallized from methanol. 0.6 g of 1-cyclopropyl-7-(4-cyclopropylmethyl-1-piperazinyl)-6-fluoro-1,4-dihydro-4-oxo-3-quinolinecarboxylic acid of melting point 279°–282° (with decomposition) is obtained.

Example 5

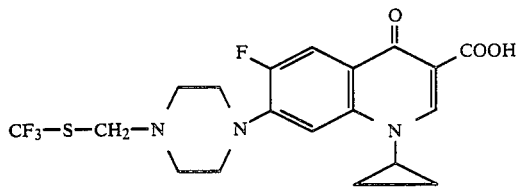

3.3 g (10 mmol) of 1-cyclopropyl-6-fluoro-1,4-dihydro-4-oxo-7-(1-piperazinyl)-3-quinolinecarboxylic acid are heated at 90° in 50 ml of dimethylformamide with 4 g (27 mmol) of trifluoromethylthiomethyl chloride, 2.1 g of triethylamine, 1.7 g of potassium iodide and 0.2 g of tetrabutylammonium iodide for 16 hours. The solution is poured into 50 ml of water and the precipitate is filtered off with suction and boiled up with methanol. 1.5 g of 1-cyclopropyl-6-fluoro-1,4-dihydro-4-oxo-7-(4-trifluoromethylthiomethyl-1-piperazinyl)-3-quinolinecarboxylic acid of melting point 247°–250° (with decomposition) are obtained.

Example 6

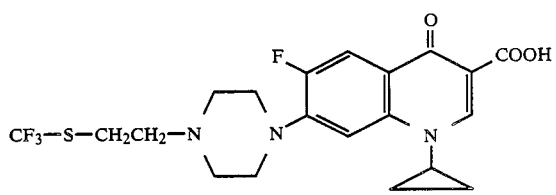

2-Trifluoromethylthio-ethyl bromide is reacted analogously to Example 5 to give 1-cyclopropyl-6-fluoro-1,4-dihydro-4-oxo-7-[4-(2-trifluoromethylthioethyl)-1-piperazinyl]-3-quinolinecarboxylic acid of melting point 188°–190° (with decomposition).

Example 7

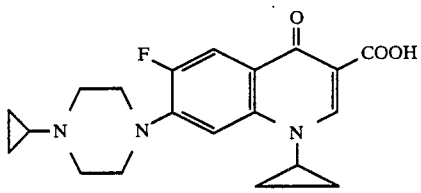

1.3 g of 1-cyclopropylpiperazine and 2.2 g (20 mmol) of 1,4-diazabicyclo[2.2.2]octane are added to 2.8 g (10 mmol) of 7-chloro-1-cyclopropyl-6-fluoro-1,4-dihydro-4-oxo-3-quinolinecarboxylic acid in 25 ml of dimethyl sulphoxide, and the mixture is heated at 140° for 5 hours. 40 ml of water are added to the suspension and the precipitate is filtered off with suction, washed with water and boiled up with 20 ml of methanol. 1.2 g of 1-cyclopropyl-7-(4-cyclopropyl-1-piperazinyl)-6-fluoro-1,4-dihydro-4-oxo-3-quinolinecarboxylic acid of melting point 226°–229° (with decomposition) are obtained.

Example 8

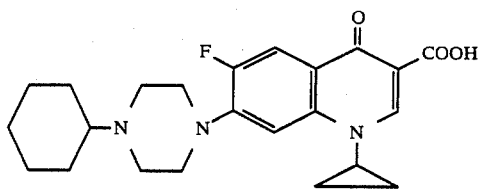

7-(4-cyclohexyl-1-piperazinyl)-1-cyclopropyl-6-fluoro-1,4-dihydro-4-oxo-3-quinolinecarboxylic acid of melting point 232°–236° are obtained analogously to Example 7 with 1-cyclohexyl-piperazine.

Example 9

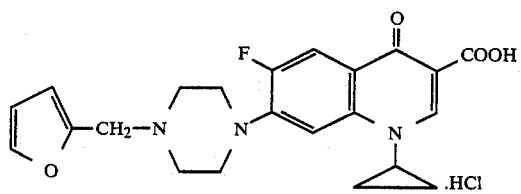

1-Cyclopropyl-6-fluoro-7-[4-(2-furylmethyl)-1-piperazinyl]-1,4-dihydro-4-oxo-3-quinolinecarboxylic acid of melting point 210°–215° (with decomposition) is obtained analogously to Example 7 with 1-(2-furylmethyl)piperazine and is converted into 1-cyclopropyl-6-fluoro-[4-(2-furylmethyl)-1-piperazinyl]-1,4-dihydro-4-oxo-3-quinolinecarboxylic acid hydrochloride of melting point 294°–297° (with decomposition) by dissolving in dilute hydrochloric acid (1:1) and precipitation with methanol.

Example 10

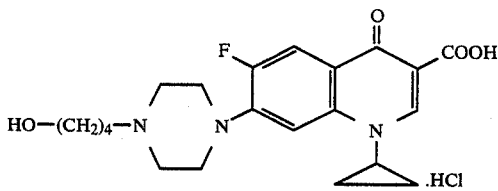

4-Chloro-1-butanol is reacted analogously to Example 5 and the reaction product is treated with dilute hydrochloric acid (1:1) to give 1-cyclopropyl-6-fluoro-1,4-dihydro-7-[4-(4-hydroxybutyl)-1-piperazinyl]-4-oxo-3-quinolinecarboxylic acid hydrochloride of melting point 325° (with decomposition).

Example 11

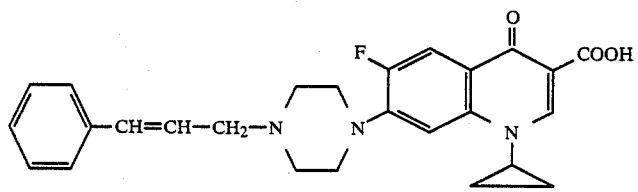

2.1 g (10 mmol) of 1-cinnamyl-piperazine and 2.2 g of 1,4-diazabicyclo[2.2.2]octane are added to 2.8 g (10 mmol) of 7-chloro-1-cyclopropyl-6-fluoro-1,4-dihydro-4-oxo-3-quinolinecarboxylic acid in 35 ml of dimethyl sulphoxide, and the mixture is heated at 140° for 5 hours. It is concentrated under a high vacuum, the residue is stirred with 50 ml of water and the pH is brought to 6 with 2N hydrochloric acid. The precipitate which has separated out is filtered off with suction, washed with water and boiled up with methanol. 1.7 g of 7-(4-cinnamyl-1-piperazinyl)-1-cyclopropyl-6-fluoro-1,4-dihydro-4-oxo-3-quinolinecarboxylic acid of melting point 230°–234° (with decomposition) are obtained.

Example 12

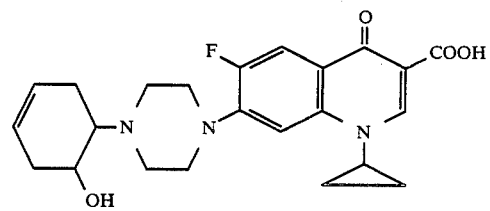

1-Cyclopropyl-6-fluoro-1,4-dihydro-7-[4-(6-hydroxy-3-cyclohexen-1-yl)-1-piperazinyl]-4-oxo-3-quinolinecarboxylic acid of melting point 277°–280° are obtained analogously to Example 11 with 1-(6-hydroxy-3-cyclohexen-1-yl)-piperazine.

Example 13

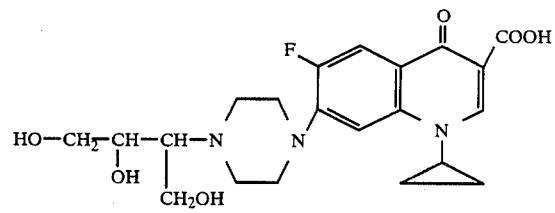

2.8 g (10 mmol) of 7-chloro-1-cyclopropyl-6-fluoro-1,4-dihydro-4-oxo-3-quinolinecarboxylic acid are heated at 140° in 30 ml of dimethyl sulphoxide with 2.5 g (11 mmol) of 1-(6-hydroxy-2,2-dimethyl-1,3-dioxepan-5-yl)-piperazine and 2.25 g (20 mmol) of 1,4-diazabicyclo[2.2.2]octane for 4 hours, the reaction mixture is concentrated, the resulting oil is diluted with 20 ml of methanol and the pH is brought to 5 with 2N hydrochloric acid. The precipitate which has separated out is recrystallized from glycol monomethyl ether/methanol. 0.5 g of 1-cyclopropyl-6-fluoro-1,4-dihydro-7-[4-(6-hydroxy-2,2-dimethyl-1,3-dioxepan-5-yl)-1-piperazinyl]-4-oxo-3-quinolinecarboxylic acid of melting point 255°–262° (with decomposition) is obtained, and is dissolved in 10 ml of 2N hydrochloric acid, with warming, to split off the protective group. After the solution has been left to stand at room temperature for 1 hour, 0.3 g of 1-cyclopropyl-6-fluoro-1,4-dihydro-7-[4-(1,3,4-trihydroxy-2-butyl)-1-piperazinyl]-4-oxo-3- quinolinecarboxylic acid of melting point 262°–268° (with decomposition) has precipitated.

Example 14

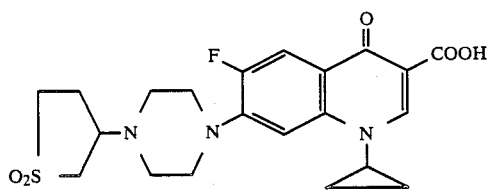

1-Cyclopropyl-7-[4-(1,1-dioxido-tetrahydrothiophen-3-yl)-1-piperazinyl]-6-fluoro-1,4-dihydro-4-oxo-3-quinolinecarboxylic acid of melting point 252°–255° (with decomposition) is obtained analogously to Example 11 with 1-(1,1-dioxido-tetrahydrothiophen-3-yl)-piperazine.

It will be understood that the specification and examples are illustrative but not limitative of the present invention and that other embodiments within the spirit and scope of the invention will suggest themselves to those skilled in the art.

What is claimed is:

1. A 1-Cyclopropyl-6-fluoro-1,4-dihydro-4-oxo-7-(1-pierazinyl)-3-quinolinecarboxylic acid of the formula

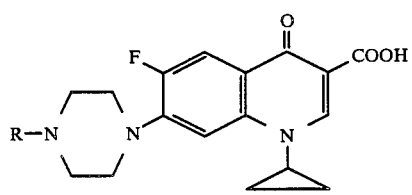

in which
R represents unsubstituted tert.-butyl, or furthermore represents 2-methylthioethyl, trifluoromethylthiomethyl, 2-trifluoromethylthioethyl, cycloalkyl with 3 to 6 carbon atoms, cycloalkenyl which has 5 or 6 carbon atoms and is alkenyl which has 5 or 6 carbon atoms and is optionally substituted by hydroxyl, 1,1-dioxidotetrahydrothiophen-3-yl, cyclopropylmethyl, 1-phenethyl or furylmethyl, or represents allyl or propargyl which is optionally substituted by phenyl,
and pharmaceutically usable hydrates, acid addition salts and alkali metal, alkaline earth metal, silver and guanidinium salts thereof, and the esters thereof.

2. A 1-cyclopropyl-6-fluoro-1,4-dihydro-4-oxo-7-(1-piperazinyl)-3-quinolinecarboxylic acid according to claim 1, in which
R represents unsubstituted tert.-butyl, or furthermore represents trifluoromethylthiomethyl, 2-trifluoromethylthioethyl, cycloalkyl with 3 to 6 carbon atoms, cyclohexenyl which is optionally substituted by hydroxyl, 1,1-dioxidotetrahydrothiophen-3-yl, cyclopropylmethyl or furylmethyl, or represents allyl or propargyl which is optionally substituted by phenyl.

3. A 1-cyclopropyl-6-fluoro-1,4-dihydro-4-oxo-7-(1-piperazinyl)-3-quinoline carboxylic acid according to claim 1 of the formula

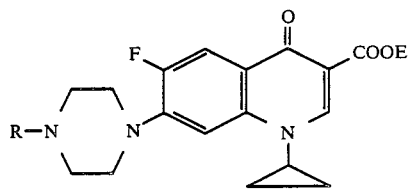

wherein
E=methyl, ethyl,

—CH$_2$—O—CO—CH$_3$, —CH$_2$—O—CO—C(CH$_3$)$_3$,

—CH(CH$_3$)—O—CO—O—C$_2$H$_5$, —CH(CH$_3$)—O—CO—CH$_3$

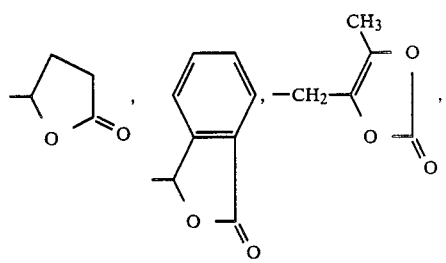

—CH$_2$—CH$_2$—N(CH$_3$)$_2$, —CH$_2$CH$_2$—N(C$_2$H$_5$)$_2$,

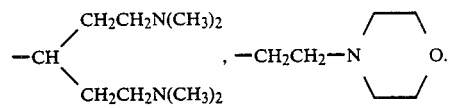

4. An antibacterial composition comprising an antibacterial effective amount of a 1-cyclopropyl-6-fluoro-1,4-dihydro-4-oxo-7-(1-piperazinyl)-3-quinolinecarboxylic acid according to claim 1 and a pharmaceutically suitable excipient.

5. A method of treating a bacterial infection in an animal or a human comprising administering to said animal or human antibacterial effective amount of 1-cyclopropyl-6-fluoro-1,4-dihydro-4-oxo-7-(1-piperazinyl)-3-quinolinecarboxylic acid according to claim 1.

* * * * *

UNITED STATES PATENT AND TRADEMARK OFFICE
CERTIFICATE OF CORRECTION

PATENT NO. : 4,806,539
DATED : Feb. 21, 1989
INVENTOR(S) : Petersen et al.

It is certified that error appears in the above-identified patent and that said Letters Patent is hereby corrected as shown below:

| | |
|---|---|
| Col. 6, line 34 | Delete "100" and substitute --10-- in second instance |
| Col. 8, line 45 | Correct spelling of --vulgaris-- |
| Col. 9, line 14 | Correct spelling of --sepsis-- |
| Col. 10, line 68 | Delete "small" and substitute --smell-- |
| Col. 19, lines 42 and 43 | Delete "alkenyl which has 5 or 6 carbon atoms and is" |

Signed and Sealed this

Thirteenth Day of February, 1990

Attest:

JEFFREY M. SAMUELS

Attesting Officer     Acting Commissioner of Patents and Trademarks